United States Patent [19]

Torgeson

[11] Patent Number: 4,622,206
[45] Date of Patent: Nov. 11, 1986

[54] MEMBRANE OXYGENATOR AND METHOD AND APPARATUS FOR MAKING THE SAME

[75] Inventor: William L. Torgeson, Pittsburgh, Pa.

[73] Assignee: University of Pittsburgh, Pittsburgh, Pa.

[21] Appl. No.: 553,854

[22] Filed: Nov. 21, 1983

[51] Int. Cl.⁴ .............................................. A61M 1/03
[52] U.S. Cl. ...................................... 422/48; 156/175
[58] Field of Search ........................ 210/321.1, 321.3; 422/45, 48; 55/158; 156/175

[56] References Cited

U.S. PATENT DOCUMENTS

| | | | |
|---|---|---|---|
| 3,034,505 | 5/1962 | Sobol | 128/214 |
| 3,413,095 | 11/1968 | Bramson | 23/258.5 |
| 3,422,008 | 1/1969 | McLain | 55/158 X |
| 3,505,686 | 4/1970 | Bodell | 3/1 |
| 3,579,810 | 5/1971 | Mon | 422/45 X |
| 3,794,468 | 2/1974 | Leonard | 23/258.5 |
| 3,864,259 | 2/1975 | Newhart | 210/88 |
| 3,893,926 | 7/1975 | Awad | 210/321 |
| 4,148,606 | 4/1979 | Morita et al. | 422/21 |
| 4,172,794 | 10/1979 | Sigdell | 210/321.3 X |
| 4,187,180 | 2/1980 | Jori | 210/321 R |
| 4,214,020 | 7/1980 | Ward et al. | 210/490 X |
| 4,224,094 | 9/1980 | Amicel et al. | 156/175 X |
| 4,401,567 | 8/1983 | Shindo et al. | 210/500.2 |

FOREIGN PATENT DOCUMENTS 523699  11/1976  U.S.S.R. .......................... 210/321.1

*Primary Examiner*—Frank Spear
*Attorney, Agent, or Firm*—Arnold B. Silverman

[57] ABSTRACT

A membrane oxygenator has a housing and a plurality of microporous hollow fibers disposed within the housing. A gas inlet and a gas outlet are in communication with the microporous hollow fibers. A blood inlet and blood outlet are so positioned that the blood flowing through the housing will flow generally transversely with respect to the longitudinal extent of the fibers. The fibers are preferably placed at a center to center spacing within a layer of about 1.5 to 4 times the diameter of the fibers. A coating, which is permeable to both oxygen and carbon dioxide, is preferably provided on the exterior of the fibers. Filaments may be positioned between at least some fibers so as to improve spacing and facilitate more efficient transfer between the gas and blood. The fibers may be wound around a frame member and adjacent layers preferably have fibers angularly offset with respect to each other. Methods and apparatus for making membrane oxygenators of the above-described types. In another embodiment, the blood may flow through the fibers and the gas around the fibers.

31 Claims, 19 Drawing Figures

MEMBRANE OXYGENATOR AND METHOD AND APPARATUS FOR MAKING THE SAME

BACKGROUND OF THE INVENTION

1. Field of the Invention

This invention relates to a membrane oxygenator and method of making the same and, more specifically, it relates to a microporous hollow fiber oxygenator and the method of making the same.

2. Description of the Prior Art

In normal healthy human beings and certain animals the lungs function as a means for transfering oxygen to the blood and receiving carbon dioxide from the blood. In many circumstances such as in certain surgical procedures, for example, the individual is unable to function in the desired manner and an oxygenator must be employed to accomplish the necessary transfer of oxygen into the blood and carbon dioxide out of the blood.

One known system of adding oxygen to the blood involves bubbling of the oxygen directly into the blood. The oxygenation process, which occurs through diffusion of oxygen from the bubbles into the bloodstream, is accompanied by diffusion of carbon dioxide from the blood into the bubbles, thus flushing excess carbon dioxide from the blood. One of the difficulties with such a system is that direct contact between the bubbling oxygen and the blood can damage the red blood cells.

It has also been known to provide semi-permeable membranes which permit passage of oxygen and carbon dioxide therethrough, thereby permitting the desired transfer without the objectionable direct contact between the oxygen gas bubbles and the blood. One of the problems which has been experienced with this approach is the fact that the transfer of gases with the blood has been inefficient.

It has also been known to employ rotating disk membrane oxygenator for effecting gas transfer. See U.S. Pat. Nos. 3,413,095 and 3,034,505.

Efforts have also been made to form the membranes into tubular shape and flow the blood through the tubes with the gasous interchange being effected through the tube wall. It has been found, however, that as a result of the rate of flow of blood as related to the permeability rates of the gases the blood flowing toward the center portions of the tube was inadequately oxygenated and inadequately relieved of the carbon dioxide. See generally U.S. Pat. Nos. 3,864,259; 3,893,926 and 3,505,686.

U.S. Pat. No. 4,187,180 discloses a hollow-fiber permeability apparatus which seeks to minimize inefficient interchange between fluid flowing along the exteriors of the hollow fibers and material within the fiber interiors. This is said to be accomplished by the use of at least one constricted portion formed in the sides of the permeating region of the hollow-fiber bundle.

U.S. Pat. No. 3,794,468 discloses a wound tubular diffusion membrane system wherein a kite winding type of approach is followed. This does not produce desired spacing and flow characteristics for such a device, in addition to being wasteful of fiber.

U.S. Pat. No. 3,413,095 discloses a disc membrane oxygenator woven glass fiber yarn is coated or impregnated with a relatively thick layer of silicone rubber.

There remains, therefore, a very substantial need for an efficiently functioning oxygenator and a method of making the same.

SUMMARY OF THE INVENTION

The present invention has met the above-described need by providing a membrane oxygenator which has a plurality of microporous hollow fibers disposed within the housing for transporting gas therethrough. Gas inlets and outlets are disposed in communication with the fibers and blood inlets and outlets are in communication with the housing in such fashion that flow of the blood across the fibers will be generally in a direction generally transverse to and preferably substantially perpendicular to the axial extent of the fibers. The spacing between fibers within a given layer is preferably, measured from center to center, about 1.5 to 4 times the diameter of the fibers.

In addition, a suitable polymeric exterior coating of a material which is permeable to both oxygen and carbon dioxide may be provided on the exterior of my hollow fibers. This serves to improve efficiency of gas transfer and improve the blood compatibility of the device.

Also, filament means may be interleaved with the fibers to produce more effective spacing to enhance efficiency of the transfer between the gas stream and the blood.

Certain preferred shapes and constructions of oxygenators of the present invention are provided. In addition, methods of and apparatus for manufacturing the oxygenators of the present invention are provided.

It is an object of the present invention to provide a hollow fiber membrane oxygenator which permits improved efficiency of gas transfer at the fiber surface.

It is another object of the present invention to provide such an oxygenator which employs a low pressure drop with respect to blood flowing through the apparatus.

It is a further object of the present invention to provide such an oxygenator which has improved blood compatibility through the use of a suitable polymeric coating on the fibers.

It is yet another object of the present invention to provide an oxygenator which has microporous hollow fibers contributing to improved transfer between the gas and the blood.

It is yet another object of the invention to provide methods and apparatus for manufacturing oxygenators of the above-described type.

These and other objects of the invention will be more fully understood from the following description of the invention on reference to the illustrations appended thereto.

DESCRIPTION OF THE DRAWINGS

FIG. 1a is a cross-sectional illustration of a portion of the oxygenator of FIG. 1 taken through 1a—1a.

DESCRIPTION OF THE PREFERRED EMBODIMENT

As used herein the term "microporous hollow fibers" shall refer to membrane fibers having a diameter generally on the order of about 0.005 to 0.02 inches, with microporous walls consisting of a very large number of submicron pores extending through the fiber wall, the pores being preferably around 0.1 micron or less in smallest dimension, and with an essentially uniform wall porosity of about 25 percent or greater.

Figure 1:
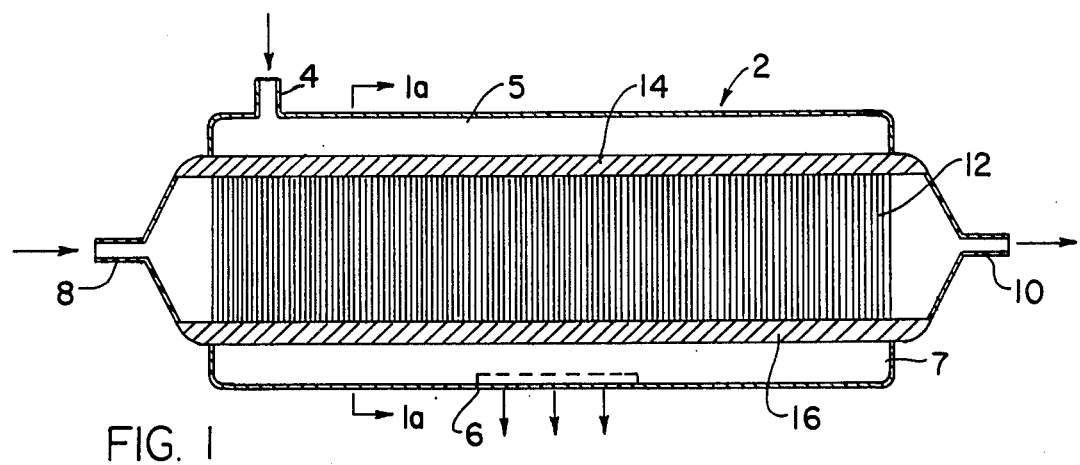
FIG. 1 is a partially schematic illustration of an oxygenator of the present invention.
Figure 1A:
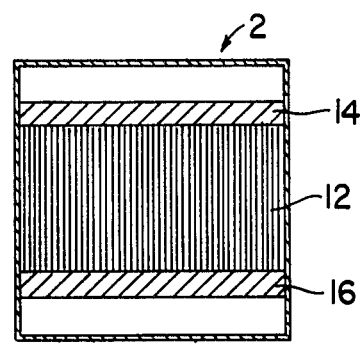

Referring now more specifically to FIG. 1 there is shown a schematic view of one form of oxygenator of the present invention. A suitable housing 2, in the form shown, has a generally rectangular cross-sectional configuration and is provided with an array of microporous hollow fibers. In the form shown the fibers are positioned generally vertically and have their ends sealingly secured to sealing material or potting material 14, 16, such as silicone rubber, or polyurethane, for example. The fibers preferably have a length of about 4 to 36 inches. The fibers or tubes 12 preferably have a length substantially less than the longitudinal extent of housing. The ends of the tubes 12 project to the upper and lower extremities respectively of the seals 14, 16. In this fashion, the gas inlet 4 which is in communication with inlet chamber 5 is in communication with the open ends of the tubes 12 thereby permitting oxygen to be introduced through the gas inlet 4 and into the tubes 12 for flow downwardly therethrough. Similarly, the lower ends of the tubes 12 are in communication with the gas outlet 6 through outlet chamber 7.

Blood entering the oxygenator through blood inlet 8 will flow generally horizontally from one end of the oxygenator to the other and emerge through blood outlet 10. In flowing through the oxygenator, it will be noted that the blood flows in a direction which is generally transverse to and preferably substantially perpendicular to the axial orientation of the fibers.

Among the preferred microporous fiber materials are synthetic polymers selected from the group including polypropylene, polyolefin and polysulfone. The fiber should preferably have a wall thickness of about 0.001 to 0.0015 inch, and external diameter of about 0.005 to 0.02 inch and have a porosity such that about 25 to 40 percent, preferably about 30 to 35 percent of the exterior surface will be open with the pores extending through the wall.

Figure 2:
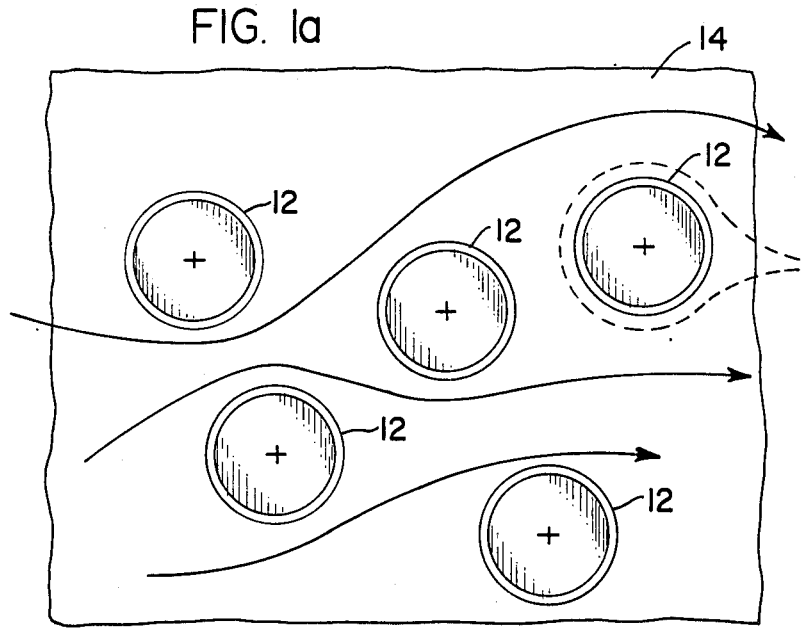
FIG. 2 is a cross-sectional illustration showing a portion of the fibers.

Referring to FIG. 2, a further feature of the invention which contributes meaningfully to improved efficiency will be considered. It is preferred in the present invention to maintain a specific spacing between adjacent fibers in the same layer, as measured center to center of about 1.5 to 4 times the external diameter of the fiber. It is also preferred to maintain this relationship with respect to fibers which are adjacent and belong to different layers or in situations where random distribution is provided. This permits efficient flow of blood (as is shown by the arrows in FIG. 2) on the exterior of the fibers while the oxygen containing fibers transfer oxygen through the fiber walls into the blood stream.

Figure 3:
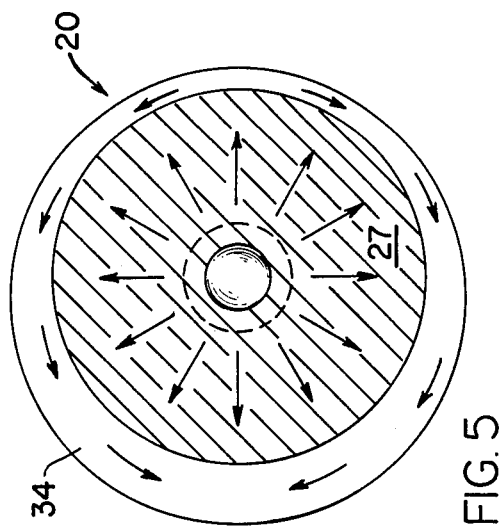
FIG. 3 is a top plan view of a modified form of oxygenator of the present invention.
Figure 5:
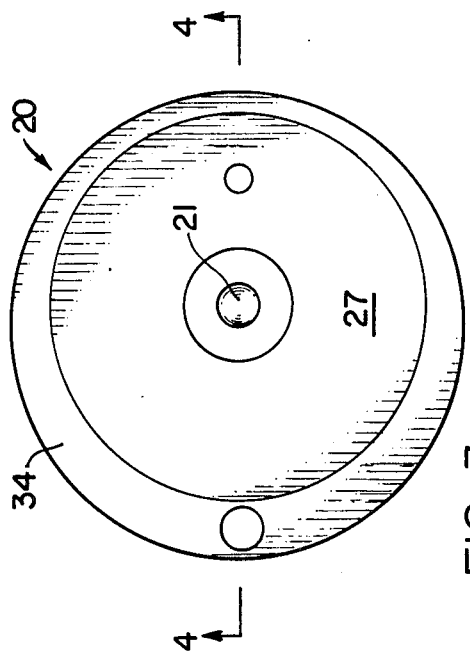
FIG. 5 is a cross-sectional illustration taken through 5—5 of FIG. 4.
Figure 4:
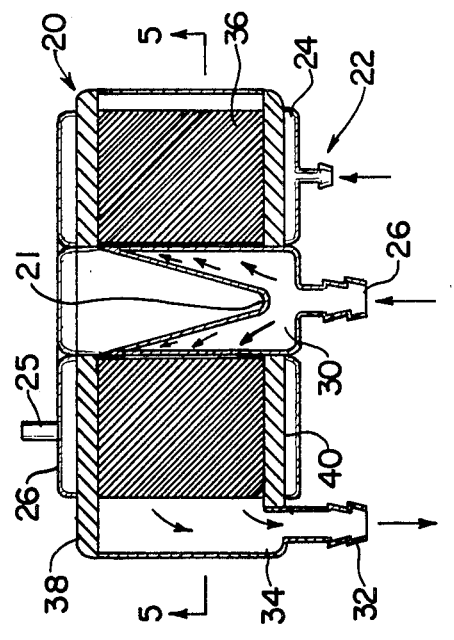
FIG. 4 is a cross-sectional illustration taken through 4—4 of FIG. 3.

Referring now in further detail to FIGS. 3 through 5, a preferred embodiment of the oxygenator of the present invention will be considered. In this embodiment the housing 20 is generally cylindrical in shape. A hub portion 30 with perforations to freely allow radial blood flow is positioned generally at the center. A gas inlet 22 is in communication with a gas inlet chamber 24. A gas outlet 25 is in communication with the gas outlet chamber 26. The exchange section 27 contains a plurality of microporous hollow fibers 36. The fibers are preferably spirally wound about the hub which contains blood inlet chamber which is defined by hub portion 30 and diffuser 21. In a preferred approach, fibers 36 may be wound generally at an angle with respect to the spool axis with a given wrap of fibers wound at a first bias angle with respect to top seal 38 and the next wrap will be wound at a reverse bias angle with respect to the top seal 38. By reversing alternate wraps in this manner, optimum flow spaces between fibers will be provided.

At the top of the fibers 36 is top seal 38 which is made of a suitable potting material which, after curing, is cut off to permit communication between the upper ends of the fibers 36 and the gas outlet chamber 26. Similarly, at the bottom, a bottom seal 40 permits cooperation between the lower ends of the fibers and the gas inlet chamber 24, while resisting communication between chambers 24, 26 and the portions of the exchange section 27 disposed exteriorly of the tubing.

Blood is introduced through blood inlet 26 and travels to blood inlet chamber 30 and then, as is shown by the arrows will move substantially horizontally across the exchange section 27 to receive oxygen passing through the microporous hollow tubes and to discharge carbon dioxide into the tubes. After travelling generally radially through the housing, the blood will be received in circumferential blood outlet chamber 34 which cooperates with blood outlet 32 in discharging the oxygenated blood therefrom. As is shown in FIG. 3, as a result of the eccentric positioning of the hub 30 within housing 20, chamber 34 is tapered.

Figure 6:
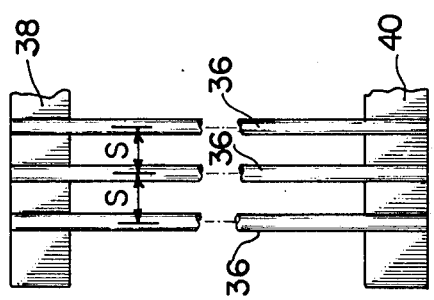
FIG. 6 is a fragmentary schematic illustration showing the relationship between several fibers in the same layer.

It is preferred that the hollow fibers have a center to center spacing S of about 1.5 to 4 times the external diameter of the fiber. This is illustrated generally as to spacing in a layer of fibers in FIG. 6.

Figure 7:
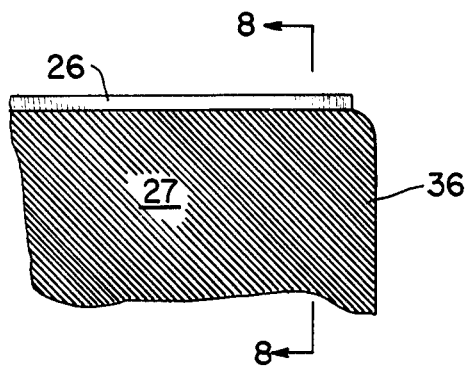
FIG. 7 is a fragmentary illustration of a portion of a gas plenum employable in the present invention.
Figure 8:
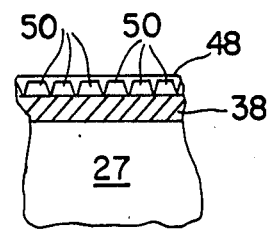
FIG. 8 is a cross-sectional illustration of a portion of the plenum of FIG. 7 taken through 8—8.

Details of a form of gas plenum shown in FIGS. 3 through 5 are illustrated in FIGS. 7 and 8. The plastic covers 24 and 26 are ribbed as indicated at 48 to define openings 50. On assembly, the ribs provide support for the potting material 38 and 40, without interfering with the gas flow, in cases where a higher than normal blood pressure is developed in the exchange region 27.

Figure 9:
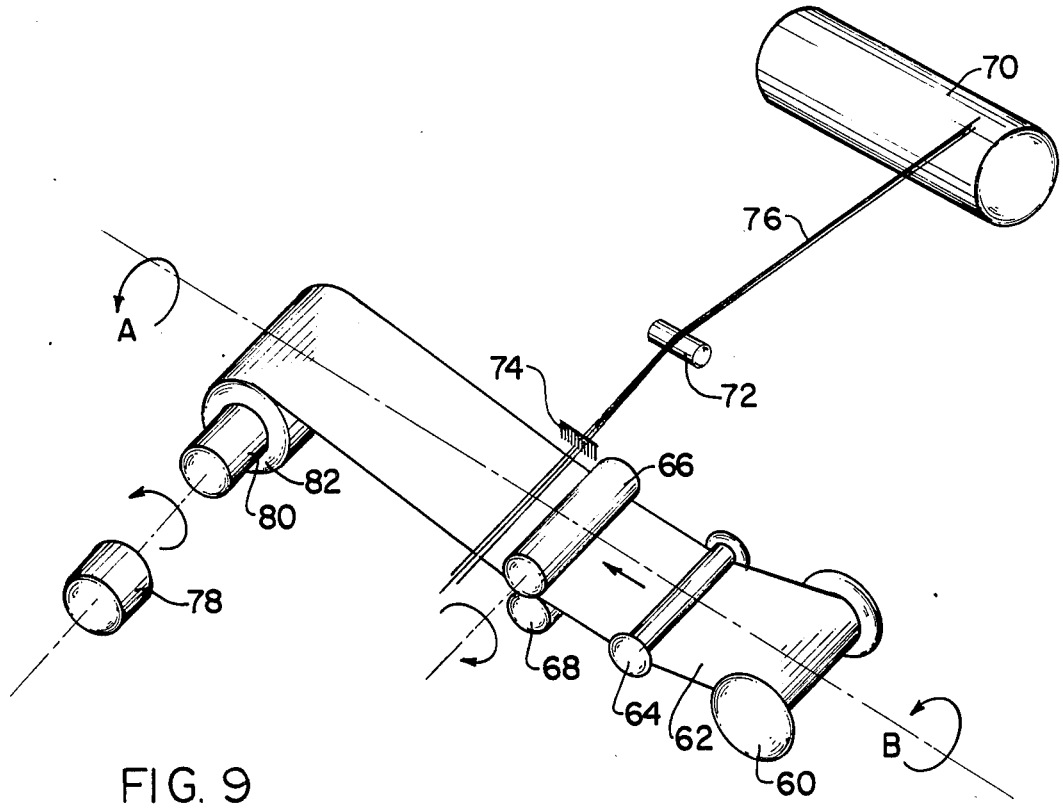
FIG. 9 is a schematic illustration of a form of apparatus usable in making an oxygenator of the present invention.

While the microporous hollow fibers may be placed in the embodiment of FIGS. 3 through 5 in any desired manner, FIG. 9 illustrates a suitable means of accomplishing this. In general, the fibers will be wound around a screen member which will in turn be coiled by winding the screen around the perforated blood inlet 30. After winding, potting material 38 and 40 is applied at the edges of the wound fibers. During the potting operation, the blood inlet 30 and the outer housing 20 are mounted in a fixture which holds them in the proper relative position. After partial curing of the potting material, the excess potting material is cut off at each edge, exposing the fiber interiors adjacent to the gas plenums 24, 26 but leaving a sealed structure in the exchange section 27. The operation of the apparatus shown in FIG. 9 is as follows: reel 60 supports a coil of screen material which is unwound through screen guide roller 64 with the aid of driven feed rolls 66, 68. A single or plurality of fibers 76, preferably the latter, is unwound from spool 70 and with the aid of fiber guide and tensioner 72 and comb 74 which serves to maintain separation between adjacent fibers causes the fibers to be wound around the screen. This is accomplished through rotation of the entire screen handling assembly which preferably has the rolls journaled in suitable members which rotate in the direction indicated by the arrows A, B. As the motor 78, through friction clutch 80, causes the rotary drive takeup reel 82 to advance the screen, the fibers will sequentially be wrapped around the advancing portions of the screen material. By removing the coiled screen containing the wrapped fibers, the potting or sealing material may be applied and subsequently severed as previously described in order to thereby establish the array of fibers. It will be appreciated that the comb openings will be so positioned as to produce the desired spacing between the microporous hollow fibers within a given layer.

Figure 10:
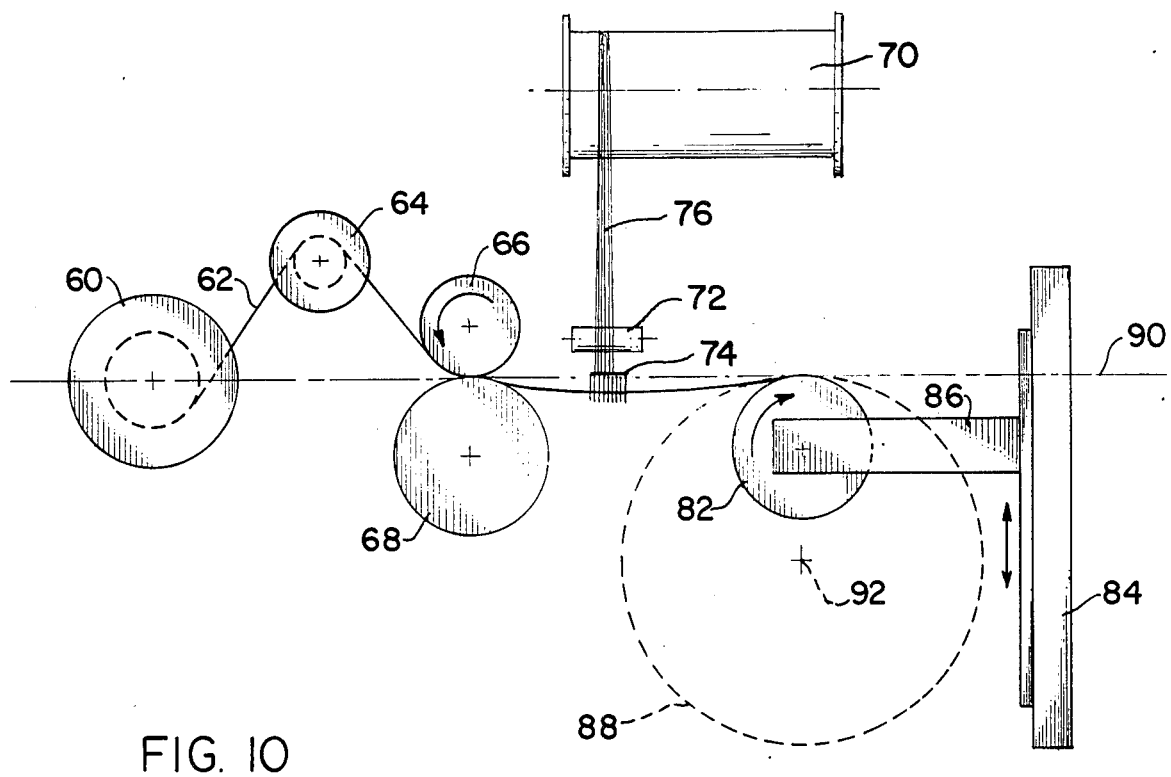
FIG. 10 is a partially schematic illustration of a form of apparatus for making a fiber matrix usable in the present invention.

FIG. 10 illustrates a slightly modified version of the apparatus shown in FIG. 9. As shown in this embodiment, the support members 84, 86 which rotatably secure takeup reel 82 are adapted for relative vertical movement. As the diameter of the fiber wrapped screen on the takeup reel increases, the support 86 will be dropped in order to maintain the takeup reel outer diameter along axis 90. This increase is illustrated in part by the additional center line 92 and dotted circle 88 each representing a later stage of wrapping.

Figure 11:
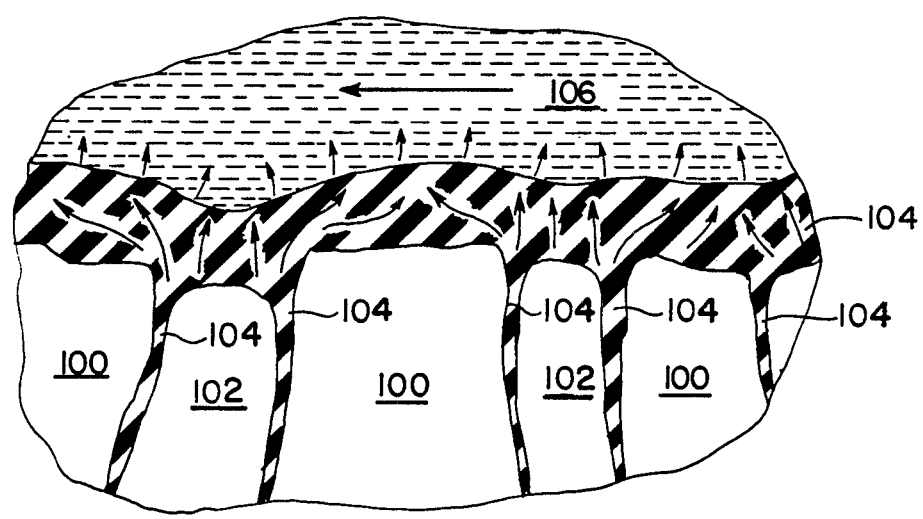
FIG. 11 is a cross-sectional illustration showing schematically a coated portion of a fiber of the present invention.

Referring again to FIG. 11 there is shown the manner in which the improved effectiveness of transfer of oxygen to the blood is achieved through the use of a synthetic polymeric resin coating on the microporous hollow fiber exterior surface. The coating is preferably selected from the group of materials consisting of silicone rubber, silicone rubber copolymers, polydimethyl siloxane, block copolymers of polydimethyl siloxane, polysulfone and fluorinated ethyl cellulose, and has a thickness of about 0.5 to 1.5 microns. The fiber wall is indicated by the number 100 and pores passing completely through the wall by the number 102 in FIG. 11. The coating material 104 is applied as a solution of the polymer in a suitable solvent or solvent system. After evaporation of the solvent, the polymer remains as a coating on the exterior surface of the fiber, bridging over the pores 102 and extending down into the pores 102, as indicated in FIG. 11. In use, oxygen enters the pores, dissolves in the coating, and passes by diffusion into the flowing blood layer 106. Use of a highly permeable coating material 104 such as silicone rubber, which has approximately seventeen times the oxygen permeability of blood plasma, facilitates the transfer of oxygen into the blood stream. It will be appreciated that in this fashion, as the oxygen passes through the pore and then throughout the coating, essentially 100 percent of the surface of the fiber will deliver oxygen to the blood regardless of whether the adjacent portion is a pore or the tube wall. Uncoated microporous membrane is subject to intrusion of blood plasma into the micropores; this results in reduced gas transport because of the resistance to gas transfer caused by the plasma "cap".

Figure 12:
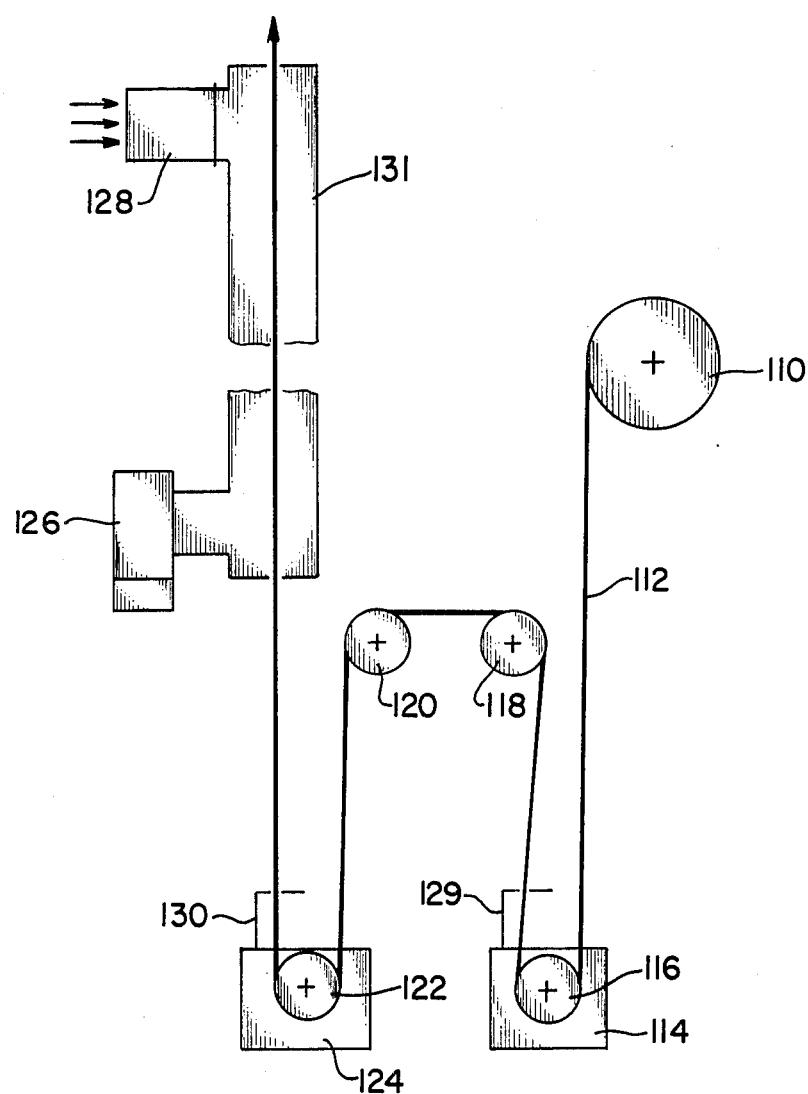
FIG. 12 shows a schematic illustration of a method of coating fibers.

Referring once again to FIG. 12 a preferred method of coating the fibers will be considered. A supply spool 110 is provided with microporous hollow fiber 112 which under the influence of guide reels 116, 118, 120, 122 passes sequentially through a cleaning solvent 114 and the coating solution 124. The solvent 114 fills the pores and the interior of the hollow fiber, excess solvent being removed by the skimmer plate 129. Prior to evaporation of the solvent from the interior of the fiber, the fiber passes through the coating solution. This coating procedure confines the coating substantially to the exterior surface of the fiber. The fiber then passes through a drying conduit 131 fitted with an inlet heater 128 and a blower 126. A skimmer plate 130 which is adapted to mechanically remove excess coating material may also be provided.

Figure 13:
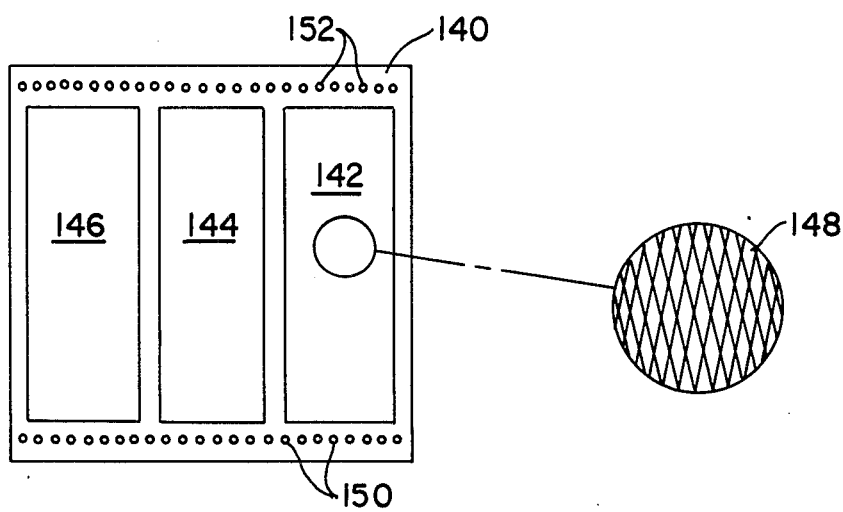
FIG. 13 illustrates a frame element of the present invention to which have been secured hollow fibers.

In the previously described embodiment, reference has been made to winding of the fiber with subsequent potting at the return bends and cutting to achieve the desired relatively short fiber lengths with exposure cooperating with the inlets and outlets for the gas. Also, in the first embodiment reference has been made to a generally vertically oriented array of fibers. As is shown in FIG. 13, the fibers may be provided by establishing a crossing pattern and securing the same to a frame. As is shown in FIG. 13, a frame member 140 has a series of openings 142, 144, 146 within which a fiber matrix 148 having the fibers angularly offset with respect to adjacent fibers is provided. A pattern of this type can be obtained by winding the fibers around the form 140, a process which can be automated easily. The fibers have their upper and lower extremities extending beyond the cutting lines 150, 152 to thereby permit securement within a sealing material and cutting to expose the inner fiber portions. A plurality of these frames may be provided in a housing in establishing the oxygenator.

Figure 14:
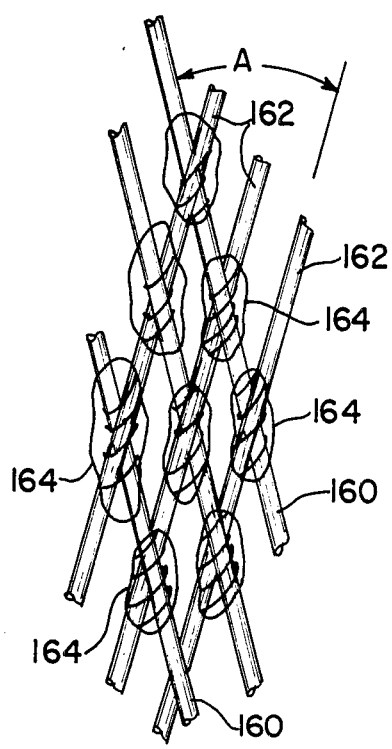
FIG. 14 is a partial illustration of a fiber matrix of the present invention.

FIG. 14 shows in greater detail a crossover pattern of fibers wherein a first series of fibers 160 in one layer are generally parallel to each other and offset from a second layer of fibers 162 with their longitudinal axes being offset from each other by an angle A. Zones 164 illustrate regions within which flow may be restricted due to fiber crossover.

Figure 15:
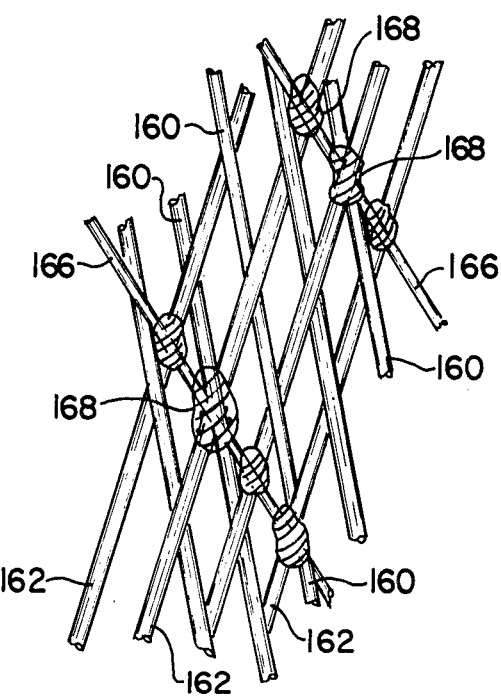
FIG. 15 illustrates a modified form of fiber matrix of the present invention.

An alternate approach to the arrangement of FIG. 14 is shown in FIG. 15. In this embodiment, which is a preferred embodiment, the fibers 160, 162 are separated by an interleaved winding of widely-spaced fibers 166. Thus, the regions of blood viscous flow retardation 164 are substantially reduced, thereby reducing the flow velocity over the balance of the fibers 160, 162 length in order to provide improved overall gas transfer. It will be appreciated that the areas of flow retardation result in increased flow velocity at other locations within the oxygenator. In general, it will be desirable to have a predetermined oxygen partial pressure at the blood outlet with the inlet velocity being less than the blood outlet velocity. This concept can easily be incorporated in the oxygenator shown in FIGS. 3–5. Preferably, these fibers 166 should be monofilament polypropylene. They may be advantageously coated with a blood-compatible coating such as silicone rubber.

Similarly, FIG. 10 illustrates how the fibers may be wound on a frame for the configuration shown in FIG. 1. In this case, a series of frames would be stacked, mounted in a housing as indicated in FIG. 1, and potted to secure the fibers in the desired matrix, with spacers (which may be in the form of interleaved fibers as indicated in FIG. 15) between frames. After curing of the potting material, the frames are cut off along the perforated "cut line" as shown in FIG. 10.

Figure 16:
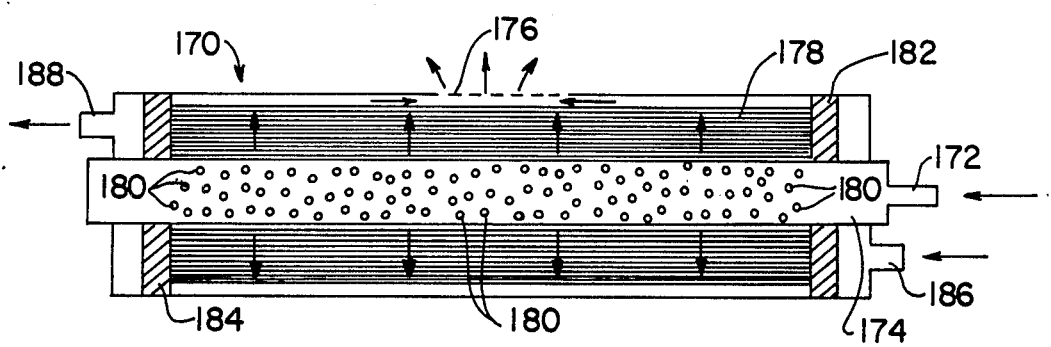
FIG. 16 is a cross-sectional, partially schematic illustration of a modified form of oxygenator of the present invention.
Figure 17:
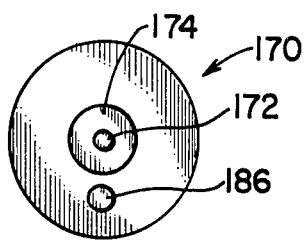
FIG. 17 is a right side elevational view of the oxygenator shown in FIG. 16.

A further modification of the invention is illustrated in FIGS. 16 and 17 wherein the blood is designed to flow within the microporous hollow fibers and the gas therearound in effecting gas exchange through the tubular membranes. The housing 170 is substantially cylindrical and has a gas inlet 172 at one end which communicates within an elongated plenum 174 which preferably covers at least a major portion of longitudinal extent of the housing and in the preferred form, as illustrated, extends the full length thereof. The plenum 174 has a plurality of openings 180 through which oxygen introduced through the inlet 172 may be discharged so as to pass over the fibers 178 and after exchange emerge through gas outlet 176. The fibers 178 run longitudinally essentially the length of the housing 170 and are secured within sealing material 182, 184, respectively at the ends thereof. Blood introduced through blood inlet 186 will travel longitudinally through the fibers and emerge through blood outlet 188.

In the embodiment of FIGS. 16 and 17, the benefits of employing a coating material such as has been described in connection with FIG. 11 may be achieved by applying the coating by suitable solvent to the interior of the fibers 178.

Interior coatings can be applied by passing the fibers through a coating solution of appropriate concentrations. The pores of the microporous fibers should be sufficiently large to allow free passage of the polymer molecules in solution.

Figure 18:
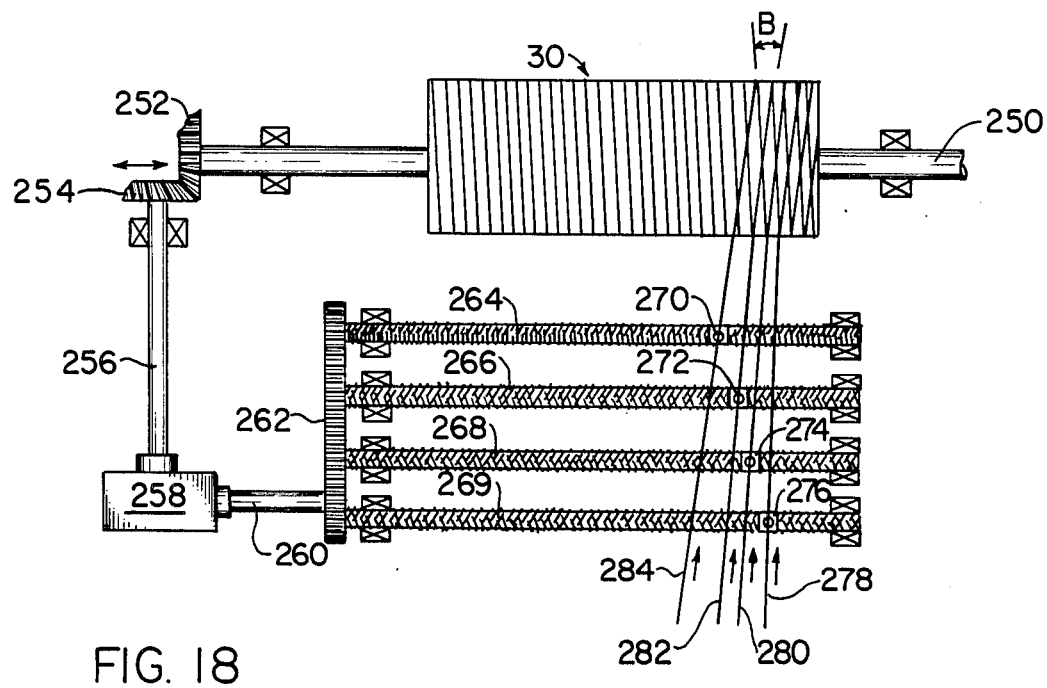
FIG. 18 is a schematic top plan illustration of a form of apparatus of the present invention.
Figure 19:
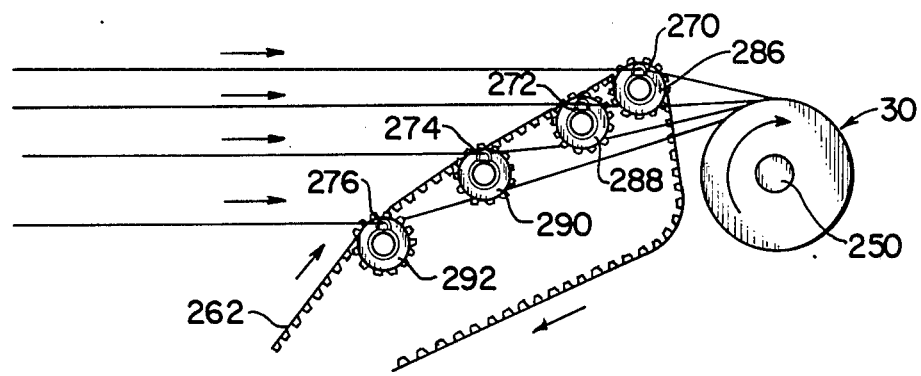
FIG. 19 is an end view of a portion of the equipment shown in FIG. 18.

While the microporous hollow fibers may be placed in the embodiments shown in FIGS. 3 through 5 in any desired manner, FIGS. 18 and 19 illustrate a preferred means of accomplishing this. As shown, the individual fibers are guided prior to winding by means of several synchronized level-winding screws, each carrying one or more fibers. The fibers are wound from side to side in alternate directions, so that the fibers of adjacent layers cross at an angle B as shown in FIG. 18. The angle B will progressively decrease as the fibers are wound. Thus, the fibers from layer to layer are non-parallel, affording advantageous contact with the blood flowing radially through the oxygenator; i.e., without shunting. FIG. 19 shows further details of the fiber winding system. Additionally, FIG. 15 shows a separate winding of monofilament fibers (also wound by means of a level-winding screw), with a wide spacing between fibers. These fibers might, for example, be spun from polypropylene and could be coated if desired with a blood-compatible material such as silicone rubber. This winding has the purpose of separating the successive layers of microporous fibers, which is advantageous from the standpoint of improved gas transfer.

Referring still to FIGS. 18 and 19, an apparatus and method for fabricating the fiber matrix of the present invention will now be considered. The fibers are wound on the perforated blood inlet chamber 30, shown in FIG. 4, which is fixedly secured to a suitably rotatably journaled shaft 250 which in turn is operatively associated with shaft 256 through bevel gears 252, 254. Shaft 250 is driven by any suitable power means (not shown) such as a motor. Shaft 256 is in turn connected to the gear train 258. The output shaft of the gear train is connected to a series of identical levelwinding screws 264, 266, 268 and 269 by means of a toothed belt 262 and sprockets 286, 288, 290 and 292. Carriage members 270, 272, 274 and 276 are threadedly secured to the screw members 264–269 and are adapted to move longitudinally therealong responsive to rotational movement of the screw members. Each carriage member has an eyelet portion through which one or more fibers pass. The carriage members may have an internally threaded tubular portion with a radially outwardly projecting eyelet portion secured thereto. The direction of the wound fibers reverses at each edge of the fiber matrix through the reversal of the direction of travel of the carriage of the individual level-winding screws. Each screw is phased relative to the others so as to cause the fibers to be essentially parallel and equally spaced in each layer. The number of screw elements will depend on the overall design of the device and is not limited to the four shown in the figures. In general, the number of fibers which are wound simultaneously is dictated by the maximum length of fiber which provides adequate gas clearance for the outermost turns.

It will be appreciated, therefore, that the present invention has provided a unique oxygenator making use of a number of means for improving the efficiency of transfer between gas and blood therein. Among the unique features employed to accomplish this objective are the use of the microporous hollow fibers, the spacing therebetween, the arrangement thereof within the housings, the use of a polymeric coating material, the use of interposed spacer filament means and the relative positioning and spacing of the fibers. There are also provided unique methods and associated apparatus for accomplishing these objectives.

Whereas particular embodiments of the invention have been described above for purposes of illustration, it will be evident to those skilled in the art that numerous variations of the details may be made without departing from the invention as defined in the appended claims.

I claim:

1. A membrane oxygenator comprising
   a housing,
   a plurality of microporous hollow fibers disposed within said housing for transporting a first fluid therethrough,
   first inlet means in communication with said fibers for delivering said first fluid thereto,
   first outlet means in communication with said fibers for receiving said first fluid therefrom,
   second inlet means and second outlet means in communication with the regions disposed exteriorly of said hollow fibers, said second inlet means being so disposed with respect to said second outlet means that a second fluid flowing through said housing will flow in a direction generally transverse to the axial extent of said hollow fibers, said hollow fibers having a wall porosity of about 25 percent or greater, said fibers being disposed in a plurality of layers, the spacing between said fibers within a said layer measured from center to center being about 1.5 to 4 times the external diameter of said fibers, whereby either gas or blood will be said first fluid and the one not so used will be said second fluid, said first fluid is blood, said first inlet means is blood inlet means, said first outlet means is blood outlet means, said second fluid is gas, said second inlet is gas inlet means, said second outlet is gas outlet means, and said fibers having an interior coating of a material which is oxygen and carbon dioxide permeable.

2. A membrane oxygenator comprising a housing, a plurality of microporous hollow fibers disposed within said housing for transporting a first fluid therethrough, first inlet means in communication with said fibers for delivering said first fluid thereto, first outlet means in communication with said fibers for receiving said first fluid therefrom, second inlet means and second outlet means in communication with the regions disposed exteriorly of said hollow fibers, said second inlet means being so disposed with respect to said second outlet means that a second fluid flowing through said housing will flow in a direction generally transverse to the axial extent of said hollow fibers, said hollow fibers having a wall porosity of about 25 percent or greater, said fibers being disposed in a plurality of layers, the spacing between said fibers within a said layer measured from center to center being about 1.5 to 4 times the external diameter of said fibers, whereby either gas or blood will be said first fluid and the one not so used will be said second fluid, said first fluid is gas, said first inlet means is gas inlet means, said first outlet means is gas outlet means, said second fluid is blood, said second inlet means is blood inlet means, said second outlet means is blood outlet means, and said fibers having an exterior coating of a material which is oxygen and carbon dioxide permeable.

3. The membrane oxygenator of claim 2 including said coating having a thickness of about 0.5 to 1.5 microns.

4. The membrane oxygenator of claim 3 including said coating material being selected from the group consisting of silicone rubber, silicone rubber copolymers, polydimethyl siloxane, block copolymers of polydimethyl siloxane, polysulfone and fluorinated ethyl cellulose.

5. The membrane oxygenator of claim 2 including said coating material resisting passage of blood therethrough.

6. The membrane oxygenator of claim 2 including said fibers being composed of a hydrophobic material.

7. The membrane oxygenator of claim 6 including said fibers being composed of a material selected from the group consisting of polypropylene, polyolefin and polysulfone.

8. The membrane oxygenator of claim 6 including said fibers being provided as woven fibers.

9. The membrane oxygenator of claim 8 including said fibers having an average length of about 4 to 36 inches.

10. The membrane oxygenator of claim 2 including said fibers having about 25 to 40 percent of the exterior surface thereof in the form of porous openings extending through the fiber wall.

11. The membrane oxygenator of claim 2 including fibers in adjacent layers being angularly offset with respect to each other.

12. The membrane oxygenator of claim 11 including filament means interleaved with said fibers.

13. The membrane oxygenator of claim 12 wherein said filament means include monofilament means disposed at an angle with respect to at least some of said fibers.

14. The membrane oxygenator of claim 2 including at least one frame element disposed within said housing, and said fibers secured to said frame element.

15. The membrane oxygenator of claim 14 including said frame members being generally rectangular with at least one opening therein, said fibers extending over said openings, and a plurality of said frame members disposed within said housing.

16. The membrane oxygenator of claim 2 wherein hollow fibers are so disposed with respect to said blood inlet means and blood outlet means that said blood flow will be substantially perpendicular to the axial extent of said hollow fibers.

17. A membrane oxygenator comprising a housing, a plurality of microporous hollow fibers disposed within said housing for transporting a first fluid therethrough, first inlet means in communication with said fibers for delivering said first fluid thereto, first outlet means in communication with said fibers for receiving said first fluid therefrom, second inlet means and second outlet means in communication with the regions disposed exteriorly of said hollow fibers, said second inlet means being so disposed with respect to said second outlet means that a second fluid flowing through said housing will flow in a direction generally transverse to the axial extent of said hollow fibers, said hollow fibers having a wall porosity of about 25 percent or greater, said fibers being disposed in a plurality of layers, the spacing between said fibers within a said layer measured from center to center being about 1.5 to 4 times the external diameter of said fibers, whereby either gas or blood will be said first fluid and the one not so used will be said second fluid, said housing being elongated and having a generally rectangular cross-sectional shape, said gas inlet means being a plenum extending over a major portion of the longitudinal extent of said housing, and said fibers being generally transversely oriented.

18. The membrane oxygenator of claim 17 including said blood inlet means being disposed at or adjacent one end of said housing, and said blood outlet means being disposed at or adjacent the other end of said housing.

19. The membrane oxygenator of claim 17 including said fibers having a length substantially less than the longitudinal extent of said housing.

20. A method of making an oxygenator comprising providing a housing having blood inlet means, blood outlet means, gas inlet means and gas outlet means, securing a plurality of layers of microporous hollow fibers having a wall porosity of about 25 percent or greater within said housing in communication with said gas inlet means and gas outlet means, positioning said blood inlet means with respect to said blood outlet means such that blood entering said blood inlet means will flow in a direction generally transversely to the axial extent of said fibers and exit through said blood outlet means, establishing spacing between adjacent fibers of said layer measured center to center of about 1.5 to 4 times the external diameter of said fibers, establishing a first layer of said fibers by simultaneously circumferentially winding a plurality of said fibers on an elongated hub member, biasing said first layer fibers at a first angle with respect to the longitudinal axis of said elongated hub, subsequently establishing a second layer of said fibers by simultaneously circumferentially winding said fibers over said first layer of fibers, biasing said second layer of fibers at a second angle with respect to said longitudinal axis of said elongated hub, winding said fiber layers such that said first angle and said second angle are sufficiently different that the fibers of one said layer are biased with respect to the fibers of said other layer, and establishing at least one additional said layer of fibers with each such additional layer having a different angle of wrap with respect to the next preceding angle.

21. The method of making an oxygenator of claim 20 including prior to assembly of said oxygenator coating the exterior of said fibers with an oxygen and carbon dioxide permeable material.

22. The method of making a membrane oxygenator of claim 21 including interposing filament means between at least some adjacent said fibers.

23. The method of making an oxygenator of claim 20 including establishing said layers of fibers by winding said fibers around a hub member, and covering the return end portions of said fiber with a sealing material and cutting through said sealing material to remove portions of said fibers and provide a plurality of fiber segments in communication of exterior of said sealing material.

24. The method of making an oxygenator of claim 23 including angularly offsetting fibers in one layer from the fibers in an adjacent layer to resist to shunting action of blood flowing therethrough.

25. The method of making an oxygenator of claim 23 including effecting winding around a screen member, and subsequently winding said screen member around a hub of a spool member prior to applying and cutting said sealing material.

26. The method of making an oxygenator of claim 25 including providing the hub of said spool as a perforated hollow member which will function as a blood inlet chamber.

27. The method of making an oxygenator of claim 23 including winding said fibers around said hub member in a generally spiral path.

28. The method of making an oxygenator of claim 20 including establishing said first layer while winding said fibers in a direction from a first end of said hub toward a second end of said hub, establishing said second layer while winding said fibers in a direction from said second end toward said first end, winding each succeeding layer in the reverse direction from the next preceding layer, and subsequently severing portions of said fibers to provide entry and exit openings therein.

29. Apparatus for manufacturing an oxygenator comprising a hub supporting rotatable shaft, power means for rotating said shaft, a plurality of rotatably mounted level-winding screws, means coordinating rotation of said screws with said hub supporting shaft, carriage means operatively associated with said screws and adapted to traverse said screws responsive to rotation of said screws, said carriage means each having at least one eyelet for passage of fibers to be wound on a hub therethrough, whereby rotation of said shaft with said fibers attached thereto will establish wrapping of said fibers about said hub, and said carriage means adapted to establish a first fiber layer when moving along said level-winding screws in a first direction and a second fiber layer biased with respect to the first fiber layer when moving along said level-winding screws in a second direction.

30. The apparatus of claim 29 including gear means interposed between said hub supporting rotatable shaft and said level-winding screws.

31. The apparatus of claim 30 including a plurality of said level-winding screws disposed in relative spaced parallel relationship to each other.

* * * * *